United States Patent [19]

Errico et al.

[11] Patent Number: 5,733,285
[45] Date of Patent: *Mar. 31, 1998

[54] POLYAXIAL LOCKING MECHANISM

[75] Inventors: Joseph P. Errico, Far Hills; Thomas J. Errico, Summit; James D. Ralph, Oakland, all of N.J.

[73] Assignee: Fastenetix, LLC, Summit, N.J.

[*] Notice: The term of this patent shall not extend beyond the expiration date of Pat. No. 5,549,608.

[21] Appl. No.: 665,402

[22] Filed: Jun. 18, 1996

Related U.S. Application Data

[63] Continuation-in-part of Ser. No. 502,285, Jul. 13, 1995, Pat. No. 5,549,608.
[51] Int. Cl.$^6$ .................................................. A61B 17/70
[52] U.S. Cl. .................................. 606/61; 606/69; 606/73
[58] Field of Search ............................. 606/61, 60, 72, 606/73, 69, 70, 71, 54, 59; 623/17

[56] References Cited

U.S. PATENT DOCUMENTS 5,261,913  11/1993  Marnay ................................ 606/61
5,443,467   8/1995  Biedermann et al. ................ 606/61
5,520,690   5/1996  Errico et al. ........................ 606/61

Primary Examiner—Guy V. Tucker
Attorney, Agent, or Firm—Joseph P. Errico

[57] ABSTRACT

A polyaxial colletted locking mechanism for use with orthopedic apparatus includes a screw, hook, or other orthopaedic implant element having a curvate head and a coupling element. The coupling element has a tapered and colletted portion having an interior chamber in which the curvate head is initially polyaxially disposed. A locking collar is disposed around the tapered and colletted portion such that translation thereof in the direction of the expanding taper causes the interior volume to contract onto the curvate head and lock it therein. The coupling element generally also includes a rod receiving recess in either the side or top thereof for for receiving a rod of the total implant apparatus. The locking collar may be caused to translate into its locking position by a mutual threading on the tapered portion and the collar, or by pressure applied to it by a separate element which locks the rod in the channel.

10 Claims, 11 Drawing Sheets

POLYAXIAL LOCKING MECHANISM

CROSS-REFERENCE TO PRIOR APPLICATION

This application is a continuation-in-part of prior application U.S. Ser. No. 08/502,285, entitled "An Advanced Polyaxial Locking Screw And Coupling Element For Use With Rod Fixation Apparatus", filed Jul. 13, 1995, now U.S. Pat. No. 5,549,608.

BACKGROUND OF THE INVENTION

1. Field of the Invention

This invention relates generally to a mechanism for polyaxially coupling and locking orthopaedic apparatus together so as to provide maximum surgical freedom and ease of use.

2. Description of the Prior Art

A variety of orthopaedic implant devices have been disclosed in the art for providing support to healing and/or fusing bone segments. These devices include bone plates, artificial joints, and rod immobilization implants. While affixation of such devices in many areas of the human body is often technically difficult, the need for variable angulability in implant devices which are used to immobilized segments of the spinal column is especially desirable. The spine is a highly complex system of bones and connective tissues which houses and protects critical elements of the nervous system and the arterial and veinous bodies in close proximity thereto. A variety of systems have been disclosed in the art which achieve this immobilization by implanting artificial assemblies in or on the spinal column.

These assemblies may be classified as anterior, posterior, or lateral implants. As the classification suggests, lateral and anterior assemblies are coupled to the anterior portion of the spine, which is the seguence of vertebral bodies. Posterior implants are attached to the back of the spinal column, generally hooking under the lamina and entering into the central canal, attaching to the transverse process, or coupling through the pedicle bone. The present invention relates to all such spinal fixation devices for immobilizing and altering the alignment of the spine by means of affixing at least one elongate rod to the seguence of selected bones.

These "rod assemblies" have a variety of pieces, including hooks, pedicle screws, and sacral blocks, each of which comprise a plurality of screws which are coupled to the rod. Pedicle screws are implanted through the posterior lateral surfaces of the laminae, through the pedicles, and into their respective vertebral bodies. The hooks are inserted under the lamina. The sacral block is coupled to the sacrum and receives the extreme end of the rod. It is the aligning influence of the rod forces the spine to which it is affixed, to conform to a more proper shape.

It has been identified, however, that a considerable difficulty may be associated with inserting screws, hooks, and sacral blocks along a misaligned curvature and simultaneously exactly positioning the rod relative thereto such that the receiving portions of sequential elements are aligned so that the rod can be passed therethrough without substantial advance contouring of the rod. Attempts at achieving proper alignment with fixed headed screws, hooks, and sacral blocks is understood to require considerably longer operating time, which is known to increase the incidence of complications associated with surgery. Often such alignments, with such fixed axes devices could not be achieved, and the entire instrumentationing effort would end unsuccessfully.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioned the rod and coupling elements, and the tedious manipulation of the many parts associated with the complex devices.

It is, therefore, the principal object of the present invention to provide a coupling mechanism, which may be incorporated into a variety of different orthopaedic devices which provides a polyaxial freedom of implantation angulation between two elements, i.e., a rod and screw.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a mechanism for flexibly coupling orthopaedic implant elements together and locking them together. The mechanism itself, which will be described more fully hereinbelow in pedicle screw, lamina hooks, and sacral block embodiments, generally comprise three primary elements. The first element has a curvate head portion; the second element has a portion thereof having a colletted and tapered exterior and an curvate interior volume for receiving the curvate head of the first element. A tapered locking collar is positioned around the tapered colletted portion of the second element such that selected translation of the collar relative to the second element causes the colletted portion to contract and the interior volume to crush lock to the curvate head.

More particularly, with respect to the pedicle screw embodiment of this invention, the polyaxial screw and coupling element assembly of the present invention comprises a bone screw having a head which is curvate in shape, for example semi-spherical, and a coupling element mounted thereon so as to be free to rotate prior to the secure fixation of the rod thereto, and which may be securely locked in a given angulation once the rod is received by the coupling element. The coupling element has a generally cylindrical main body portion, a locking collar, a removable external rod securing sleeve, and a top locking nut.

The coupling element may be conceptually divided into a lower socket portion, and a rod and nut receiving portion. In a first embodiment, in which the rod is received into the side of the coupling element, the rod and nut receiving portion may be subdivided into the intermediate rod receiving portion and the top nut receiving portion. (In the alternative embodiment in which the coupling element receives the rod from the top, the subdivision is unnecessary.)

The lower socket portion includes an interior chamber having an opening at the bottom thereof. The interior chamber is ideally suited for receiving therein the head of the screw such that the screw and the coupling element are held together in a rotationally and angularly free relationship. The external surface of the socket portion includes at least one vertical slot which is provided so that the opening in the bottom of the element may expand to receive the head of the screw, which has a major diameter which is larger than the unexpanded opening, such that the head of the screw may enter into the interior chamber. The at least one slot resiliently expands to permit the head of the screw to enter, and subsequently contracts into its original position once the head is fully inserted, therein inhibiting the screw head from being retracted. The head of the screw and the interior chamber are, however, free to rotate and angulate relative to one another.

The exterior of the lower socket portion of the coupling element, into which the screw head is inserted, tapers outward slightly toward the bottom of the element, therein having a slightly wider diameter at the bottom than at the top thereof. A locking collar, having a diameter equal to, or slightly larger than the top of the lower portion, but less than the diameter of the bottom of the lower portion, is initially disposed about the coupling element with the bottom of the locking collar resting against the widening surface of the element. The top of the collar may include two opposing grooves, or notches, onto which the rod is initially placed. Displacement of the locking collar downward causes the at least one vertical slot in the lower socket portion of the coupling element to narrow, therein causing the inner surface of the interior chamber to move radially inward, contacting the head of the screw, and locking thereto, thereby inhibiting further swingability.

The intermediate portion of the coupling element comprises a side receiving channel wherein the rod of the implant apparatus is mounted. More particularly, at a position above the lower portion, a channel is formed in the side of the generally cylindrical body, therein providing a receiving locus into which a support rod may nest. In order that the rod may be securely held within the receiving locus, an external rod securing sleeve is provided. The external rod securing sleeve is generally cylindrical in shape, having a hollow center for sliding over the top of the coupling element. The bottom of the cylindrical sleeve may include opposing grooves, similar to the grooves in the top of the locking collar. The grooves are positioned and designed to mate with the top of the rod, and to lock thereto upon the application of a downward force. The grooves of the sleeve, however, are preferably deeper than those of the locking collar, enabling the sleeve to encompass a larger angular section of the rod, thereby securely locking the rod in the rod receiving locus between the grooves of the sleeve and the grooves of the locking collar. In addition, the receiving locus is necessarily wider than the rod which is to be placed therein. This dimension relationship is required so that the sleeve may be forced down onto the rod, and that the rod may in turn force the locking collar downward. The rod, therefore, must be able to translate downward relative to the coupling element, within the receiving locus.

The upper portion of the coupling element comprises a threading onto which a locking nut may be inserted, therein providing a downward force onto the rod securing sleeve. The downward force of the sleeve is translated to a downward force of the rod, and on the locking collar. The locking collar is forced downward by the rod, and locks the screw in the interior chamber of the coupling element.

Each portion of the coupling element (lower, intermediate, and upper) includes a central bore, aligned with one another and which extends axially from the top of the coupling element into the interior chamber. The screw head correspondingly includes a recess, which is alignable with the central bore of the coupling element, whereby a screw-driving instrument may be inserted through the central bore, into the recess in the screw, and utilized to drive the screw into the bone.

The first step in the process of implanting this embodiment of the invention is to insert the head of the screw into the interior chamber of the coupling element. Once it has been inserted, the angle of insertion at which the screw will have the greatest holding strength relative to the loading which the rod system will be applying thereto must be determined. Once this angle has been found, the screw and the coupling element are aligned with respect to one another so that a screw-driving tool may be inserted down the central bore of the coupling element, into the recess in the head of the screw, and thereby be rotationally inserted into the bone. Subsequent to the insertion of the screw, the screw-driving device is removed from the assembly, therein permitting the coupling element to rotate and change angular alignment relative to the screw.

In this position, the locking collar of the coupling element has not yet been forced downward to lock the screw to the coupling element. The top of the locking collar extends upward, beyond the top of the lower section, and is disposed above the lower lip of the receiving channel. The rod of the implantation apparatus is then provided into the side receiving locus, and is positioned so that it rests snugly within the opposing grooves of the top of the locking collar. Once the rod has been properly positioned the securing sleeve is placed onto the coupling element, with the top of the rod resting in the opposing grooves thereof. The top locking nut is then introduced onto the top of the coupling element.

The final act of driving the top locking nut down onto the upper portion of the coupling element causes the rod securing sleeve to fully descend, therein translating the rod and the locking collar therebelow downward, locking the rod between the two pair of grooves of the sleeve and the locking collar, respectively, and causing the locking collar to secure the angulation of the coupling element to the head of the screw.

It shall be understood that the securing sleeve may extend downward far enough to engage the locking collar as well, adding to the force which causes the collar to translate down and crush lock the head of the screw within the interior volume.

In a second embodiment of the pedicle screw, the rod is received from the top of the coupling element. The coupling element may be conceptually divided into a lower socket portion, and a top rod receiving portion. The socket portion is the same as in the first embodiment. The top rod receiving portion of the coupling element comprises a central channel formed vertically downward into the body of the coupling element. More particularly, from a position above the lower portion, a section of the generally cylindrical body which extends upward therefrom is removed therein providing a receiving locus into which a support rod may nest. The top portion of the coupling element, therefore, comprises a U-shape, the inner surfaces of the top portion being spaced apart sufficiently to receive the support rod therein. In other words the upper portion comprises a pair of upwardly extending members, spaced laterall from one another, between which members is a U-shaped channel.

In this embodiment, in order that the rod may be securely held within the receiving locus, an external rod securing sleeve as above may be provided. In the alternative, the top locking nut may be sufficient. The exterior surface of the uppermost section of the top rod receiving portion of the coupling element comprises a threading onto which a locking nut may be inserted, therein locking the rod and/or the securing sleeve onto the coupling element. The bottom surface of the nut is designed to mate with either the top edge of the rod securing element or directly to the rod. It is the engagement of the nut with the upper portion of the coupling element, and the driving of the nut downward onto the upper portion of the securing sleeve or the rod which causes the rod to be locked in position. The rod is, therefore, locked between the curvate bottom of the U-shaped rod receiving locus, and the curvate top of the U-shaped rod securing sleeve or the nut itself.

As stated above, with respect to the first embodiment, the bottom edge of the rod securing sleeve and/or the rod itself are designed to mate with the upper surface of the locking collar. When the nut is driven downward, therein driving the rod securing sleeve and/or rod downward as well, the locking collar descends as described above with respect to the side loading embodiment, locking the screw within the curvate interior volume.

In alternate embodiments, the polyaxial colletted taper locking mechanism may be used in side or top loading lamina hook assembly. The assembly comprises a curvate flat blade portion which has a ball shaped head. The corresponding coupling element, of the side or top loading embodiments set forth above, is mounted on the ball shaped (semi-spherical) head so that it is rotationally free prior to secure fixation of the rod thereto, and which is securely locked in a given angulation once the rod is received by the coupling element.

Subsequent to proper positioning of the blade portion of the hook under the corresponding lamina, the coupling of the rod to the coupling element (as set forth in more detail hereinabove), and the setting of the proper angulation of the coupling element relative to the hook, the locking collar is forced by a sufficient application of pressure downward along the exterior of the lower portion of the coupling element. The locking collar therein applies an inward force against the walls of the interior chamber, and the corresponding narrowing of the vertical slots thereof. Once fully driven downward the locking collar causes the coupling element to be securely locked relative to the blade portion of the hook.

An alternate implant device which may utilize the polyaxial colletted locking coupling element mechanism of the present invention is a sacral block. This embodiment of a sacral block includes a flat plate-like first element, which may be affixed to the sacrum by a pair of bone screws. This first element includes a ball head element disposed above the plate surface, onto which the corresponding coupling element (side or top loading) may be mounted.

In each of the embodiments described above, the inner surface of the locking collar and the outer surface of the lower socket portion of the coupling element may alternatively comprise mateable threadings, oriented such that rotation of the locking collar relative to the coupling element causes the collar to translate down the lower portion toward the bottom of the element. In these embodiment, therefore, the locking collar may be independently driven downward along the lower socket portion of the coupling element to lock the curvate head of the first element in the interior volume of the second.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1A:
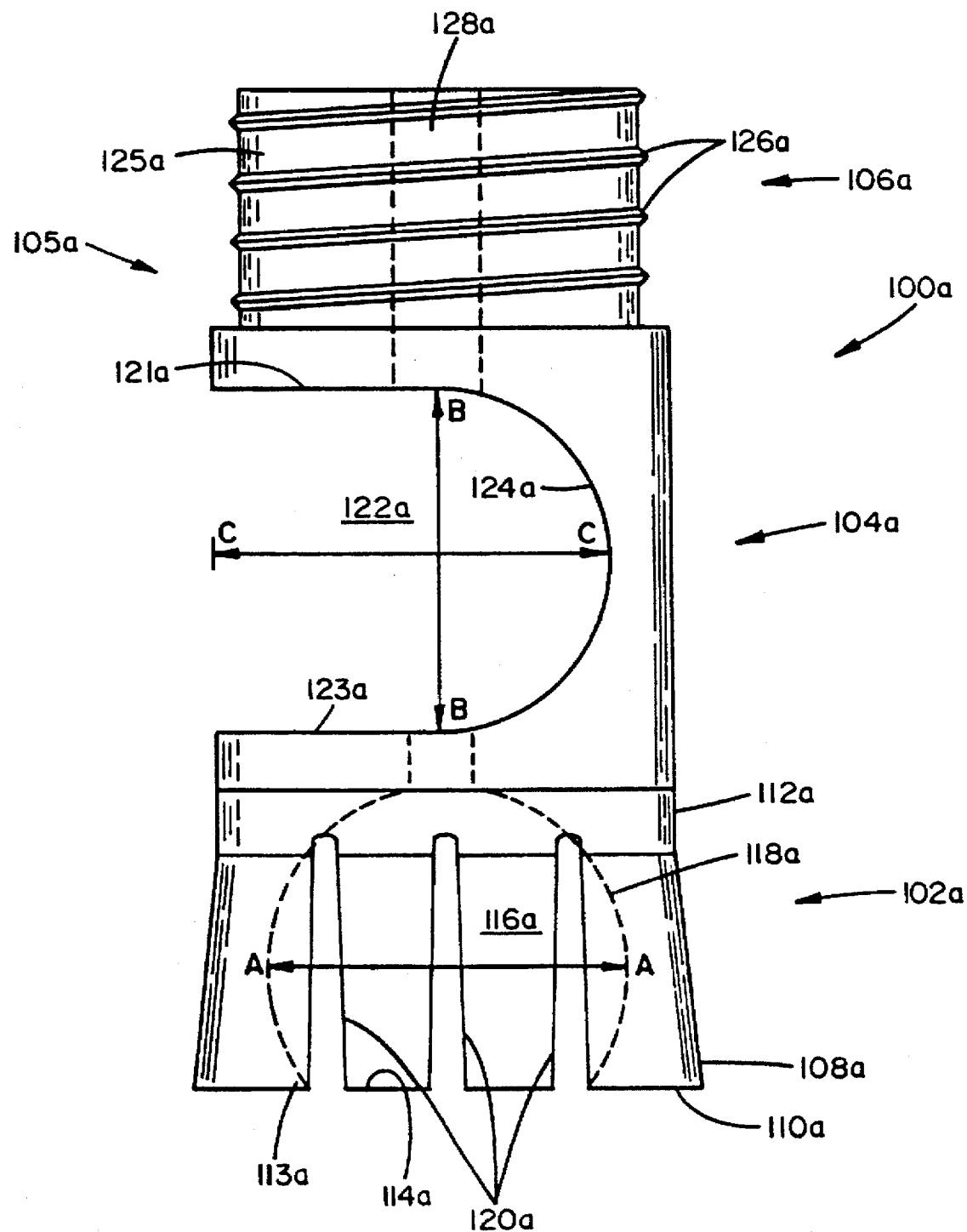
FIGS. 1a and 1b are, respectively, side views of the side and top loading coupling elements of the present invention.
Figure 1B:
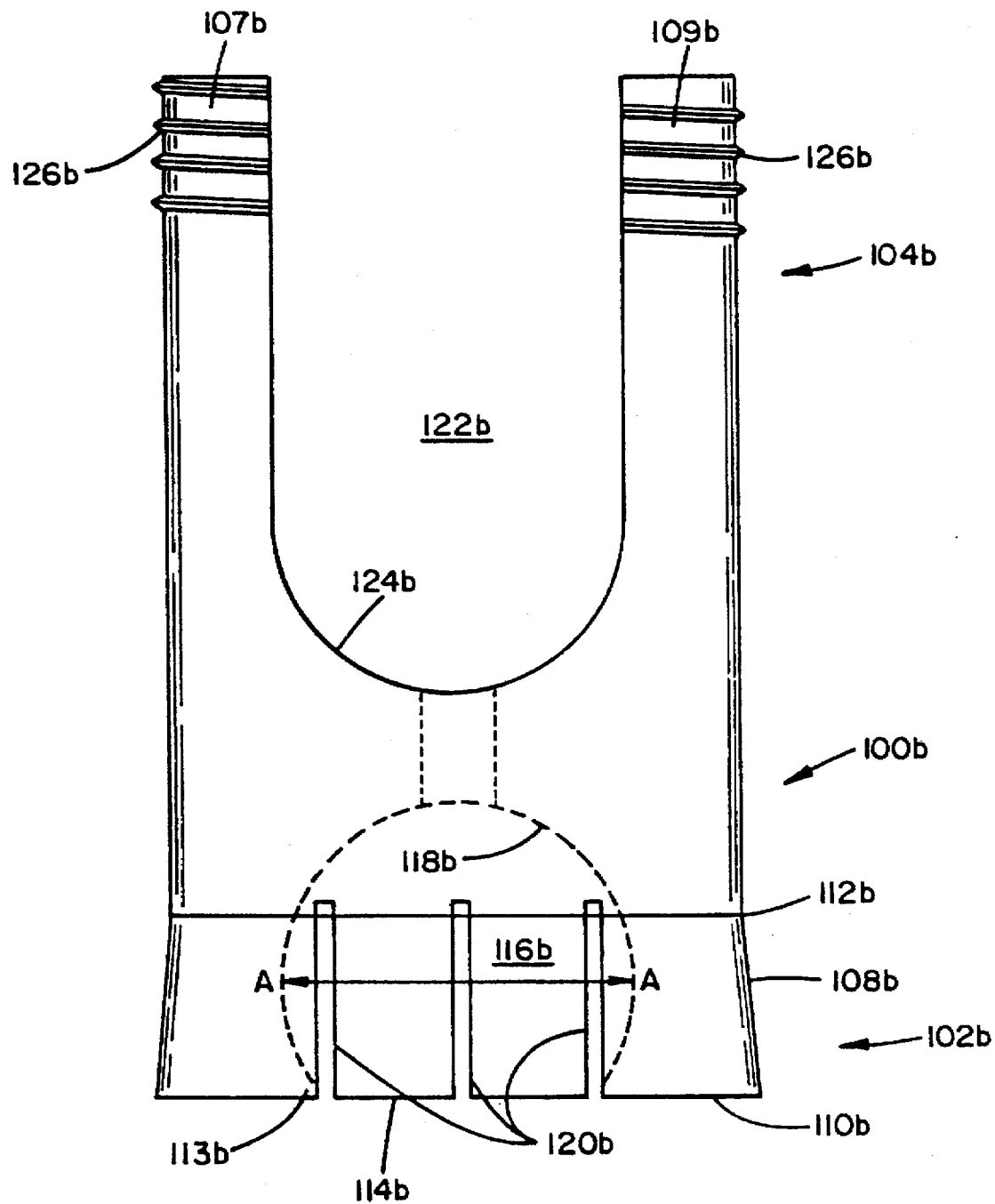

Referring now to FIGS. 1a and 1b, alternative preferred embodiments of the coupling element 100a,100b of the present invention is shown in side views, wherein critical features of the interior of the element are shown in phantom. The coupling elements 100a,100b each comprise a generally cylindrical body which may be conceptually separated into a lower portion 102a,102b and an upper portion 106a,106b, each of which shall be described more fully hereinbelow. The upper portion 106a of the coupling element 100a shown in FIG. 1a, may be further subdivided into an intermediate portion 104a and a top portion 105a.

First, with respect to the lower portions of each element 102a,102b, which are identical, the exterior surface 108a, 108b of the body is tapered in the elongate direction such that the body is wider at the bottom 110a,110b of the lower portion 102a,102b than at the top 112a,112b thereof. The bottom 110a,110b of the element 100a,100b includes an opening 114a,114b, defined by annular lip 113a,113b, which forms the mouth of an interior chamber 116a,116b. The diameter of the opening 114a,114b, when otherwise unaffected by external deflecting forces, is more narrow than the maximum diameter A—A of the interior chamber 116a, 116b. The interior chamber 116a,116b has a generally curvate inner surface 118a, 118b which is correspondingly shaped to receive a semi-spherical shaped object.

The exterior surface of the lower portion 102a, 102b includes a series of slots 120a,120b which extend vertically upward from the bottom 110a,110b of the element 100a,100b to a point which is closer to the top 112a,112b of the lower portion 102a,102b than the maximum horizontal diameter A—A. The slots 120a,120b are provided in order that the application of an external deflecting force may widen or narrow the opening 114a,114b therein permitting the insertion of an object which is larger than the undeflected diameter of the opening 114a,114b or conversely, providing for the retention of an object which is smaller than the undeflected diameter of the opening 114a, 114b.

With specific reference to FIG. 1a, the intermediate portion 104a of the generally cylindrical body of the coupling element 100a includes a large horizontal channel 122a, a rod receiving locus, in the side of the coupling element 100a. The channel 122a comprises a curvate inner wall 124a. In the embodiment shown in FIG. 1a, the vertical distance B—B from the top 121a of the channel 122a to the bottom 123a thereof, is larger than the diameter of the rod which is to be provided therein. This distance B—B is necessarily larger than the diameter of the rod so that the rod may be translated upward and downward within this channel 122a. In addition, the maximum channel vertical dimension C—C is such that the support rod which is positioned therein nests fully within the coupling element 100a, and does not extend beyond the lateral extent thereof (which would prevent a rod securing sleeve, as shall be described with reference to FIG. 4 from sliding into retaining relationship with the rod within the channel 122a).

Further with respect to FIG. 1a, the top portion 105a of the coupling element 100a comprises a slightly narrower cylindrical core 125a, having a threading 126a thereon. This top portion 105a, and the threading 126a thereon, is ideally suited for receiving a top locking nut (see FIG. 3).

Additionally, an axial bore 128a extends through the top portion 105a, through the intermediate portion 104a, and into the lower portion 102a. The bore 128a provides a linear passage through which a user may insert a screw-driving tool to access the ball head in the interior chamber 116a, and any structural elements therein.

Referring now to FIG. 1b, upper portion 104b of the generally cylindrical body of the coupling element 100b comprises a pair of upwardly extending members 107b,109b defining therebetween a vertically oriented channel 122b in the top of the coupling element 100b. The channel 122b comprises a curvate bottom surface 124b which, for example defines a semi-circular cross-section. The depth of the channel 122b is such that a support rod which is positioned therein may nest fully within the coupling element 100b, the top of the rod thereby being positioned substantially below the top of the upper portion. This permits the top locking nut (see FIG. 3) to be disposed on the top of the coupling element in a manner described more fully hereinbelow.

The upper portion 104b of the coupling element 100b, which comprises a pair of spaced apart upwardly extending members 107b,109b also comprises an external surface threading 126b. These members 107b,109b, and the threading 126b thereon, are ideally suited for receiving a top locking nut (see FIG. 3).

Figure 2:
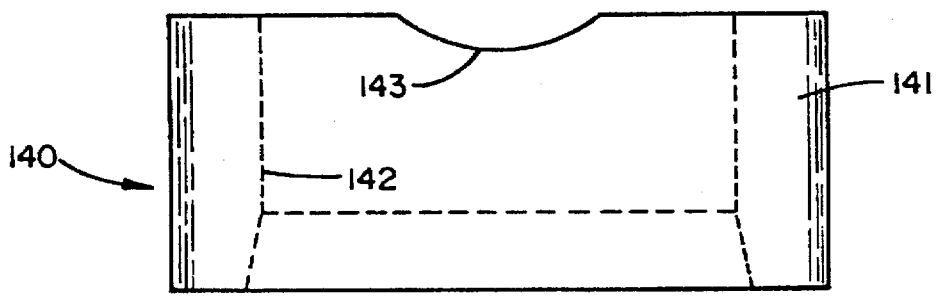
FIG. 2 is a side view of the locking collar of the present invention, shown along a direction wherein the rod seating grooves thereof are aligned perpendicular to the plane of view.

Referring now to FIG. 2, the locking collar 140 comprises a short and hollow tubular body 141 having a pair of opposing grooves 143. The grooves 143 are provided for the rod to seat against in the collar's initial disposition. The interior surface 142 of the locking collar 140 also includes a taper. The collar 140 is designed to translate downward along the lower portion 102a,102b of the coupling element 100a,100b to cause the contraction of the interior volume 116a,116b, thereof, thereby locking therein a ball which had previously been polyaxially retained therein. The mutual tapering of the collar 140 and the lower portions 102a,102b of the coupling elements 100a,100b eliminates means by which the relative motion of the collar 140 and the coupling element 100a,100b may bind before causing the crush locking of the ball in the interior volume 116a,116b.

Figure 3:
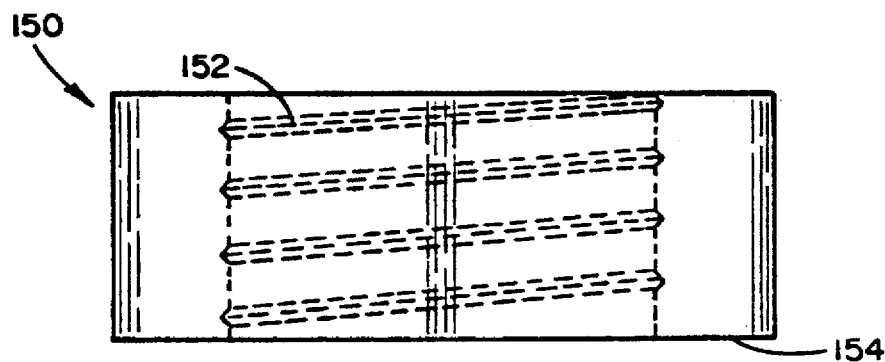
FIG. 3 is a side view of the top locking nut which is an aspect of the present invention.

Referring specifically to FIG. 3, the top locking nut 150 comprises an inner threading 152 which is intended to mate with the threading 126a,126b on the upper portions 106a, 106b of the coupling elements 100a,100b. The bottom surface 154 of the nut 150 is intended to seat against either the top surface of the rod, or against the top surface of the rod securing sleeve (see FIGS. 4 and 8a) but is permitted to rotate relative to the sleeve, therein providing a means for driving the sleeve and/or rod downward (as more fully described hereinbelow with respect to the full assembly of the device, and with respect to FIGS. 8a and 8b).

Figure 4:
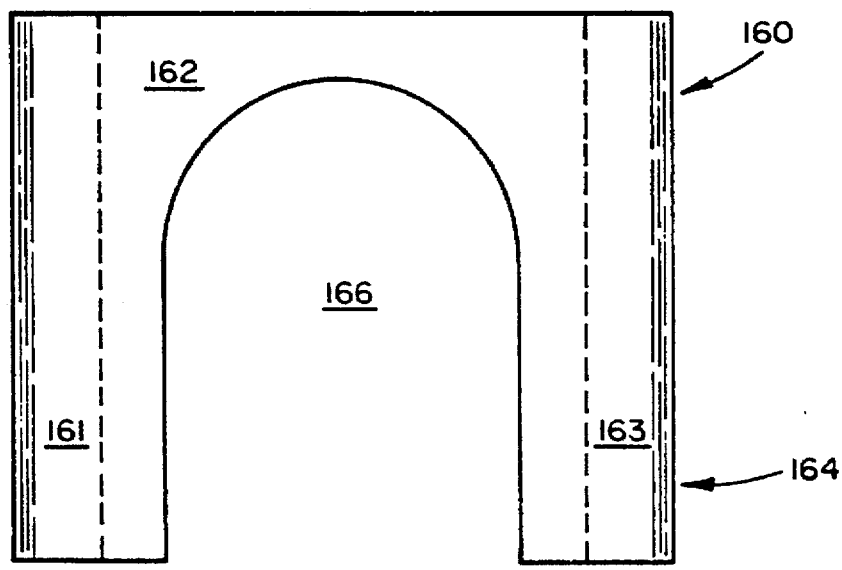
FIG. 4 is a side view of a rod securing sleeve which is utilized in embodiments of the present invention.

Referring now specifically to FIG. 4, and the rod securing sleeve 160 shown therein, the sleeve comprises a hollow cylindrical body 162 having an interior diameter which is equal to the outer diameter of the coupling element 100a, so that it may be placed thereover. The bottom portion 164 of the rod securing sleeve 160 comprises a pair of downwardly extending members 161,163 which define, therebetween, a second channel 166 through which the rod passes. The rod securing sleeve is therefore, introduced over the upper portion 106a of the coupling element 100a, once the rod has been inserted in the side channel 122a thereof. The downward translation of the rod securing sleeve 160 causes the rod to translate downwardly within the channel 122a, along with the locking collar 140, until the locking collar 140 locks the ball head in the interior volume 122a of the coupling element 102a, and the rod is locked in the channel 122a.

Figure 5:
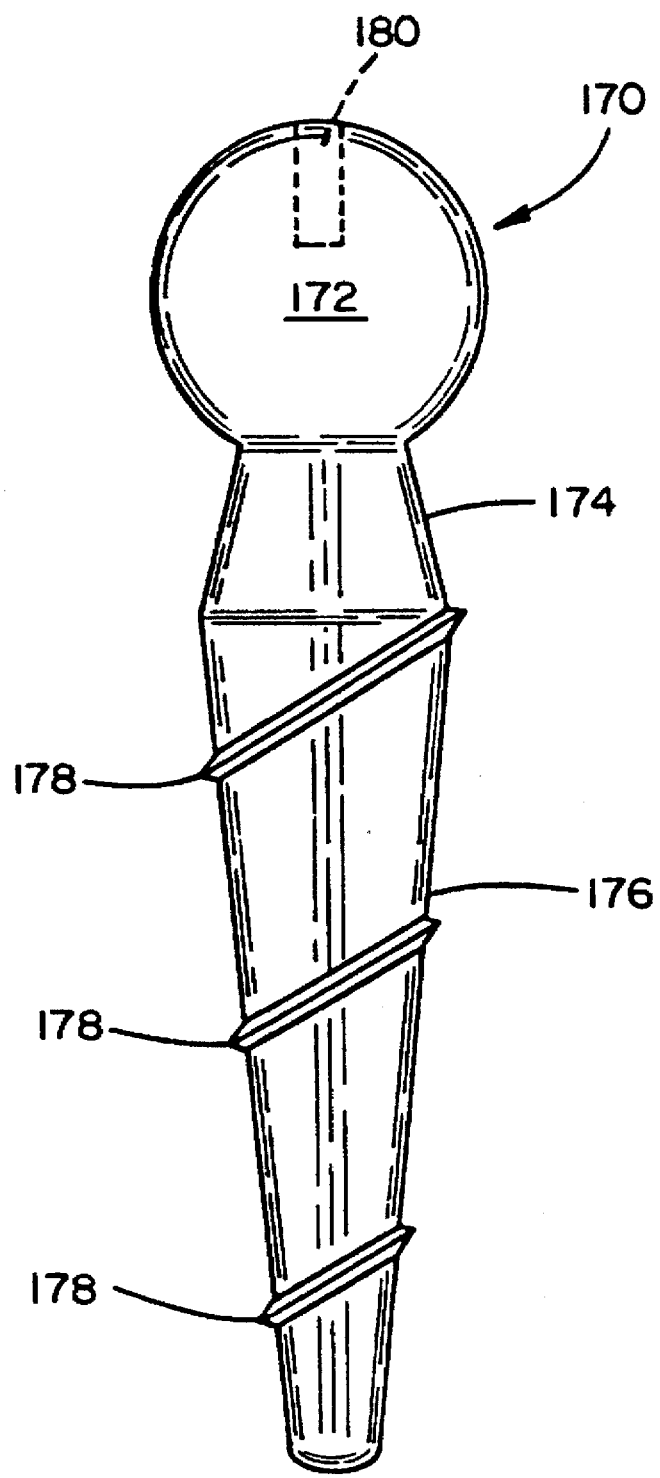
FIG. 5 is a side view of the pedicle screw which is an aspect of certain embodiments of the present invention.

Referring now to FIG. 5, a side view of the screw portion of the present invention, comprising a curvate head is shown. The screw 170 comprises a head portion 172, a neck 174, and a shaft 176. In FIG. 5, the shaft 176 is shown as having a tapered shape with a high pitch thread 178. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 172 of the screw 170 comprises a semi-spherical shape, which has a recess 180 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 172 (as shown in the two dimensional illustration of FIG. 5) includes at least 270 degrees of a circle.

The recess 180 defines a receiving locus for the application of a torque for driving the screw 170 into the bone. The specific shape of the recess 172 may be chosen to cooperate with any suitable screw-driving tool. For example, the recess 180 may comprise a slot for a flat-headed screwdriver, a crossed recess for a phillips head screwdriver, or most preferably, a hexagonally shaped hole for receiving an allen wrench. It is further preferable that the recess 180 be co-axial with the general elongate axis of the screw 170, and most particularly with respect to the shaft 176. Having the axes of the recess 180 and the shaft 176 co-linear facilitates step of inserting the screw 170 into the bone The semi-spherical head portion 172 is connected to the shaft 176 at a neck portion 174. While it is preferable that the diameter of the shaft 176 be less than the diameter of the semispherical head 172, it is also preferable that the neck 174 of the screw 170 be narrower than the widest portion of the shaft 176. This preferable dimension permits the screw to be locked at a variety of angles while still being securely joined to the coupling element.

Figure 6:
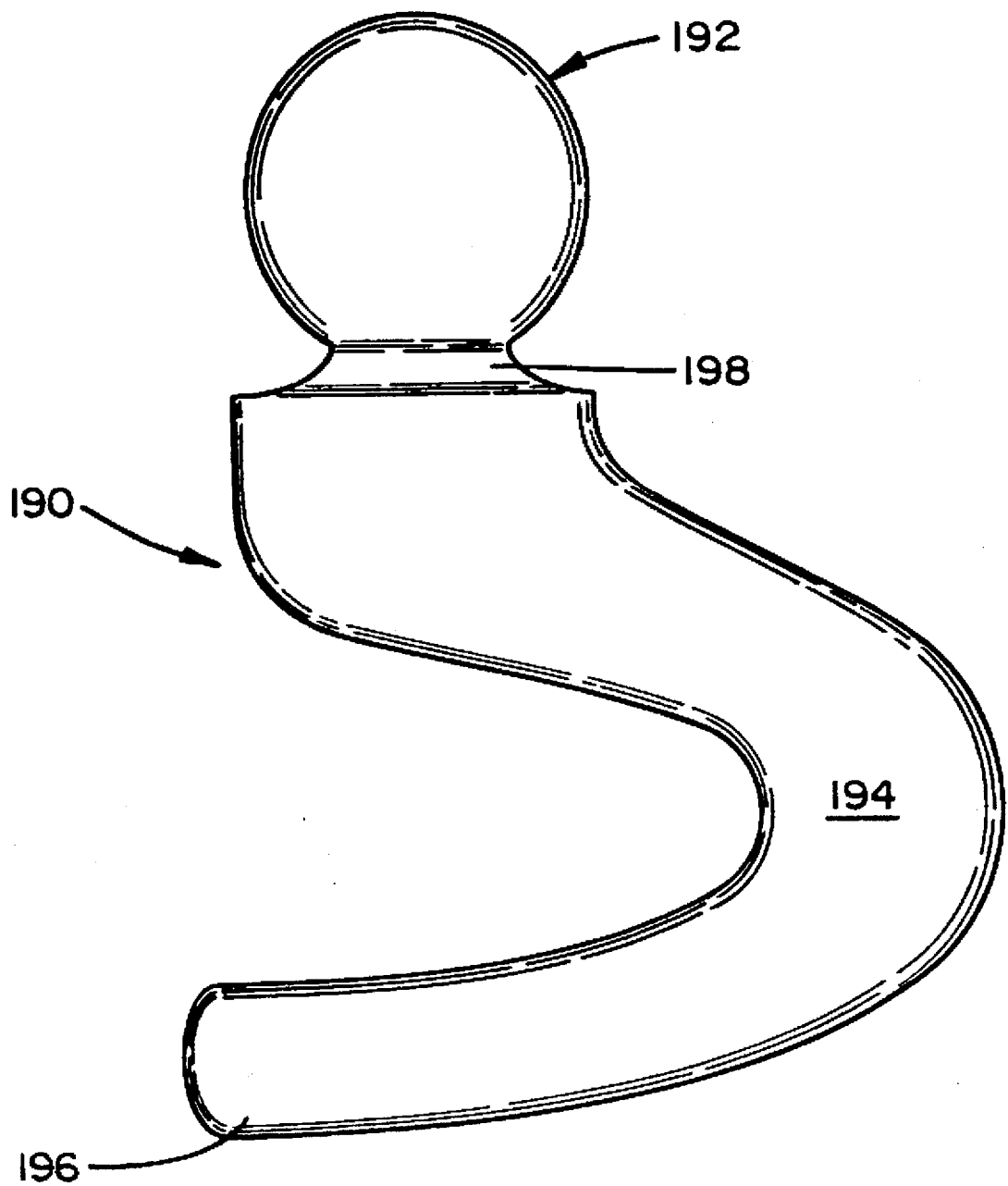
FIG. 6 is a side view of the blade portion of the lamina hook aspect of the present invention.

Referring now to FIG. 6, a side view of the blade portion 190 of the hook device is provided. The blade portion 190 comprises a head portion 192 and a C-shaped portion 194. The lower extending branch 196 of the C-shaped portion 194 comprises a flat member which is understood to be the portion which is inserted under the lamina of the patient's spine. The semi-spherical head portion 192 is connected to upper extending branch of the C-shaped portion 194 at a neck portion 198.

The head portion 192 of the blade portion comprises a semi-spherical shape. It is understood that the semi-spherical shape is a section of a sphere. In the embodiment shown, the section is greater in extent than a hemisphere, and it correspondingly exhibits an external contour which is equidistant from a center point of the head. In a preferred embodiment, the major cross-section of the semi-spherical head 192 includes at least 270 degrees of a circle.

Figure 7:
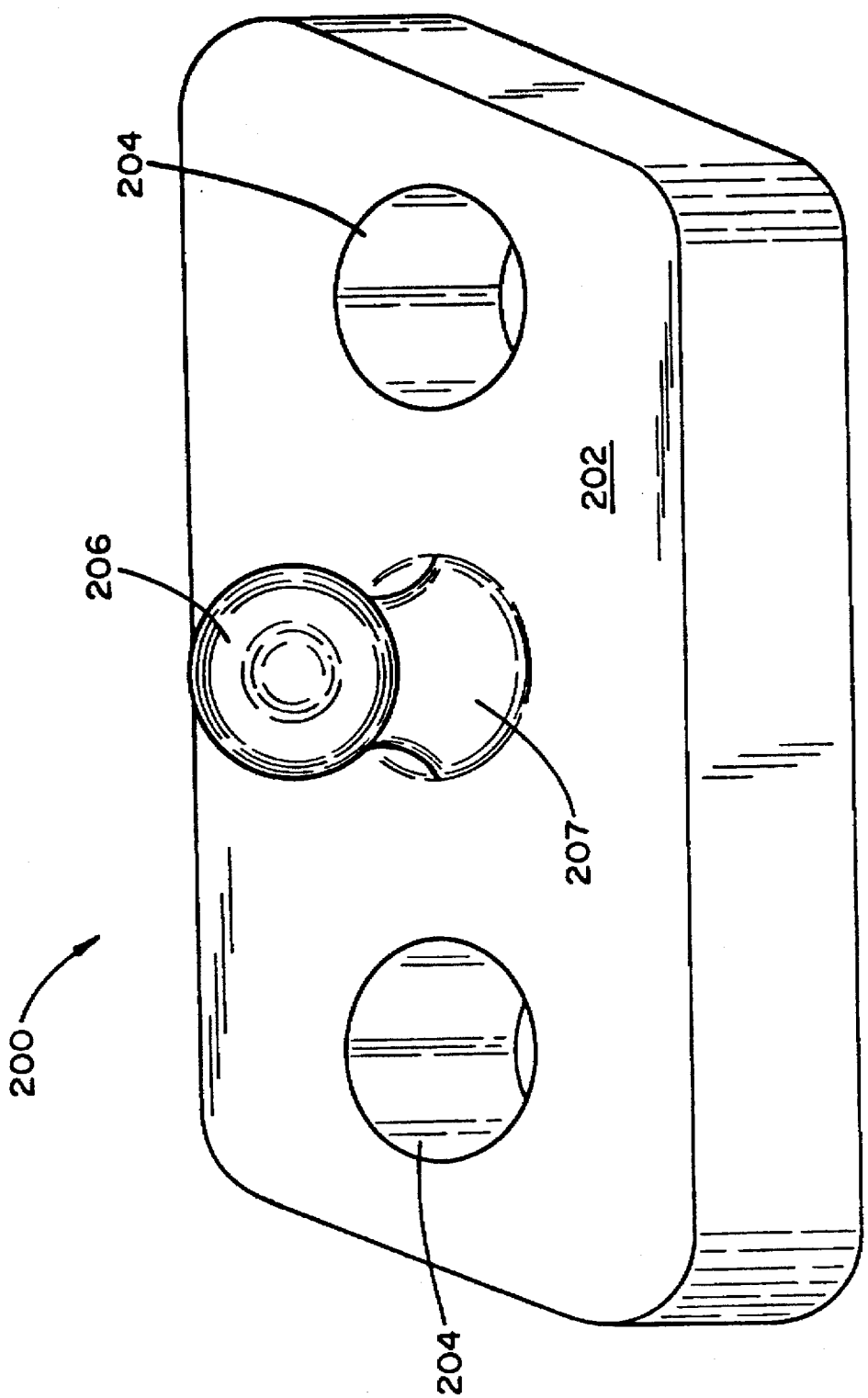
FIG. 7 is a side view of the plate portion of the sacral block aspect of the present invention.

Referring now to FIG. 7, a side perspective view of the sacral block 200 is provided. The block 200 comprises a generally planar portion 202 having a pair of through holes 204 therein for receiving therethrough bone screws so that it may be secured to a sacrum. It further includes an upwardly projecting semi-spherical ball 206, which is mounted on a wide short post or neck 207. This semi-spherical ball 206, as are the semi-spherical ball heads of the screw and blade 172 and 192, respectively, is provided for insertion into, and subsequent locking within, the interior volume 116a,116b of the polyaxial coupling element 100a,100b.

Figure 8A:
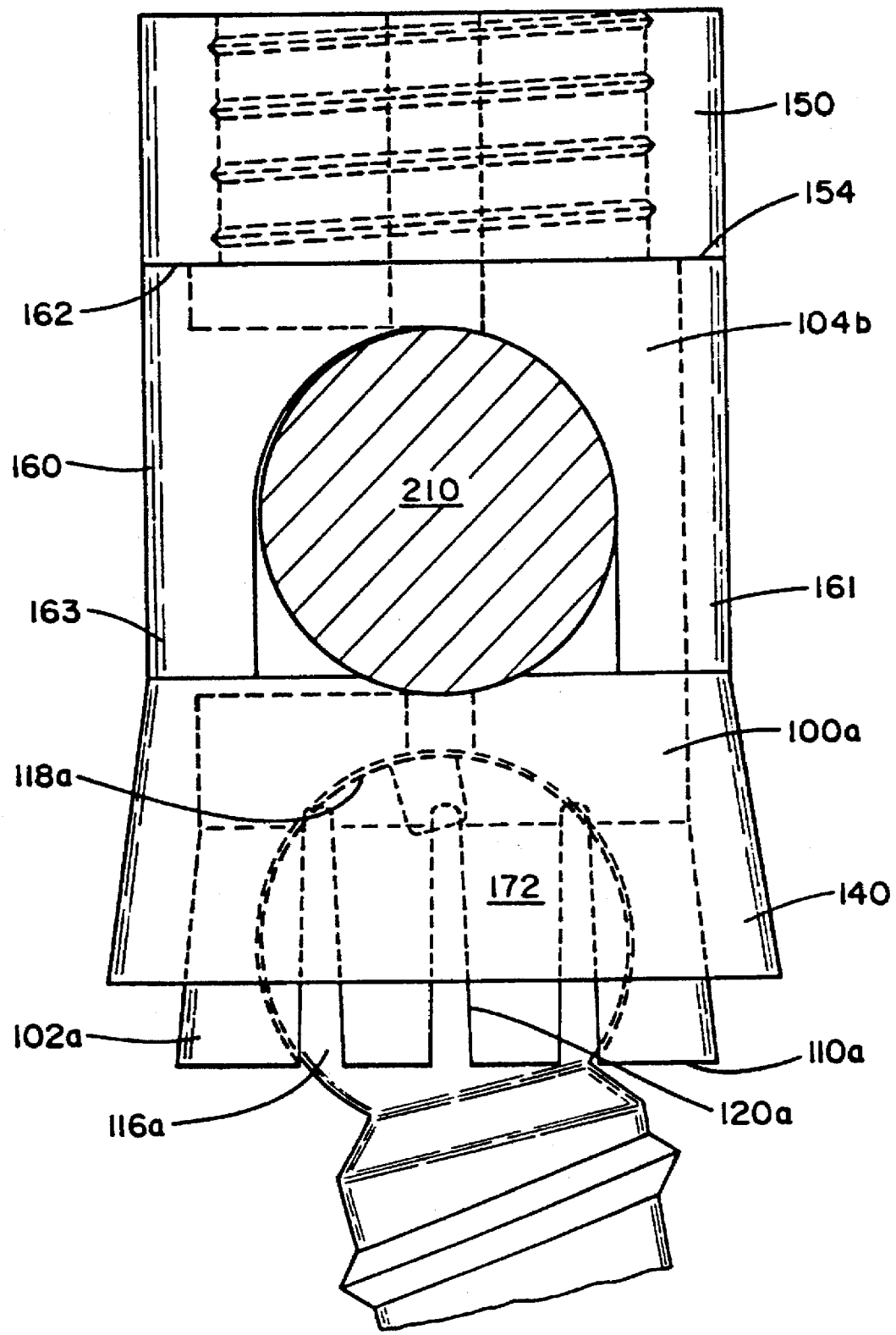
FIGS. 8a and 8b are, respectively, side views of the coupling elements of FIGS. 1a and 1b, mounted on ball head of the type illustrated FIGS. 5, 6, and 7 including the locking collar of FIG. 2, the locking nut of FIG. 3, the rod securing sleeve FIG. 4, and a rod.
Figure 8B:
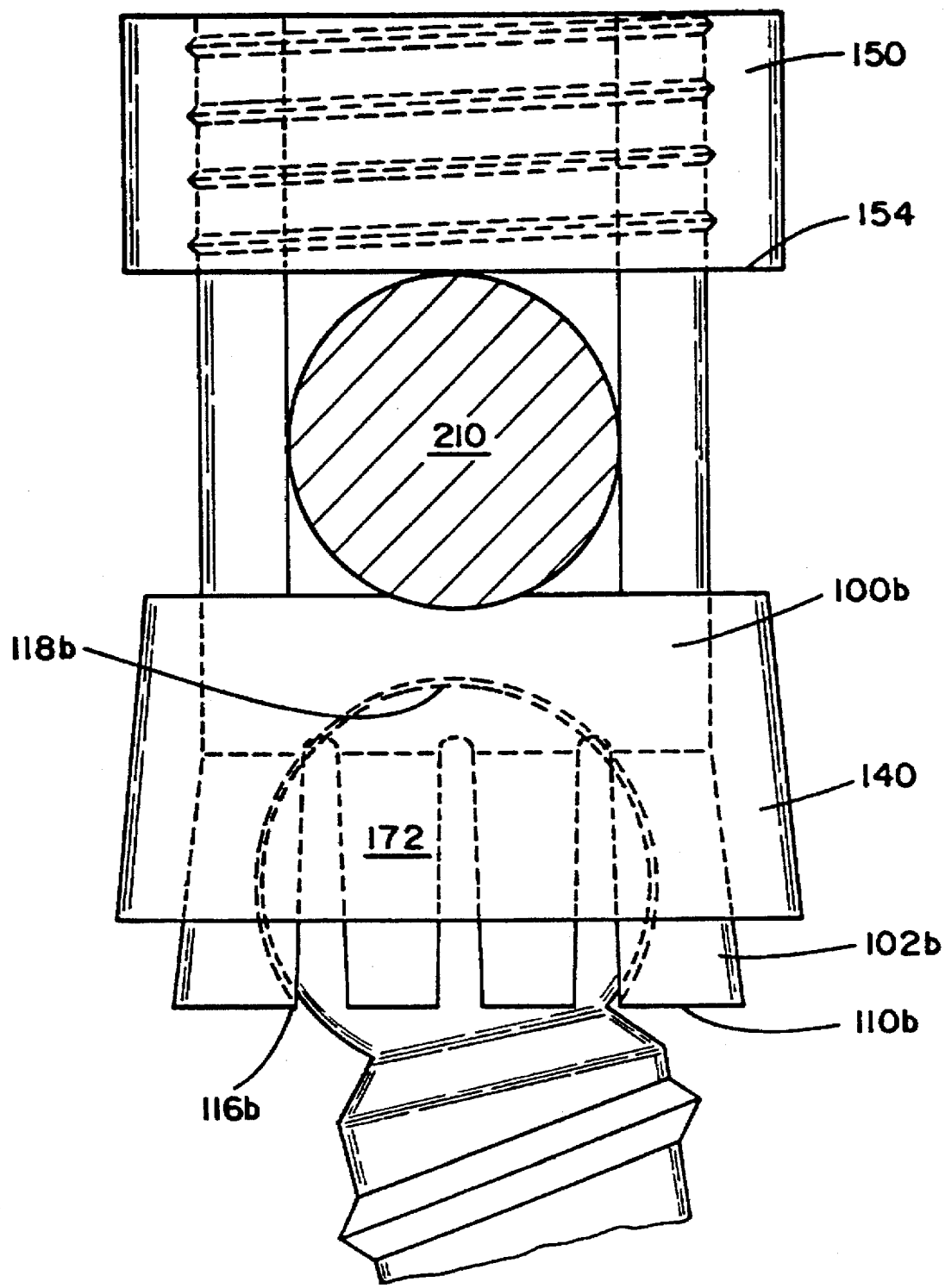

Referring now to FIGS. 8a and 8b, the coupling elements 100a and 100b, as described more fully above with respect to FIGS. 1a and 1b, respectively, are shown in side views. In these views: (1) a semi-spherical ball head 172,192,206 of the screw 170 or blade 190 or block 200 has been received within the interior chamber 116a,116b; (2) the locking collar 140 is shown in its locked position about the lower portion 102a,102b; (3) the top locking nut 150 is threaded onto the upper portion 104a,104b; and (4) on the side loading coupling element 100a only, the rod securing sleeve 160 has been positioned over the coupling element 100a to retain the rod in the element.

Prior to full assembly, the head 172, 192, or 206 of corresponding elements, is free to move polyaxially relative to the coupling element 100a,100b, however, it is prevented from fully separating from the interior chamber 116a,116b by the annular lip 113a,113b at the bottom 110a,110b of the lower portion 102a,102b.

Implantation of these implant devices is preceded by the proper preparation of the implantation site. (For example, with a pedicle screw embodiment, a pre-drilled hole is provided in the bone, into which it is desired that the screw 170 may be inserted.) The head 172,192,206 is inserted into the interior chamber 116a,116b of the coupling element 100a,100b. As stated above, at this point in the assembly process, the locking collar 140 has not yet been forced downward along the outwardly tapered lower portion 102a, 102b, thereby permitting rotational and polyaxial relative motion.

Once the coupling element 100a,100b and the ball head are properly aligned, the screw, hook, or sacral block is affixed to the appropriate prepared site and the support rod 210 is nested within the channel 122a,122b, and disposed on the grooves 143 of the locking collar 140. In the case of the side loading coupling element 100a, the rod securing sleeve 160 is then dropped over the element 100a, such that the grooves 143 of the sleeve 160 are seated against the top of the rod 210. In the top loading embodiment 100b, the rod securing sleeve 160 is not necessary.

With either embodiment, once the proper angulation of the coupling element to the head 172,192,206 and the secure nesting of the rod 210 in the channel 122a,122b on the locking collar 140 have been established the top locking nut 150 is threaded onto the threading 126a,126b of the upper portion 106a,106b.

In the side loading embodiment 100a, the bottom surface 154 of the nut 150 seats against the top surface 162 of the rod securing sleeve 160. As the nut 150 is advanced, and descends relative to the coupling element 100a, the rod securing sleeve 160 is driven downward. This motion causes the rod 210 to translate downward therein forcing the locking collar 140 to descend as well. The locking collar 140 may be driven downwardly by either interaction solely with the rod 210, or also by direct contact with the downwardly extending members 161,163 of the rod securing sleeve 160.

In the top loading embodiment 100b, in which the rod securing sleeve 160 is not utilized, the top locking nut 150 is advanced directly into contact with the rod 210, which in turn causes the collar 140 to descend.

In either case, by descending along the tapered lower portion 102a,102b of the element, the locking collar 140 provides an inwardly directed deflecting force which causes the slots 120a,120b in the lower portion 102a,102b of the element to narrow so that the collar may proceed downward This deflection inward causes the inner surface 118a,118b of the interior chamber 116a,116b to crush lock against the head 172,192,206. This clamping force locks the angulation of the screw, hook, or block 170,190,200 to the coupling element 100a,100b.

Figure 9A:
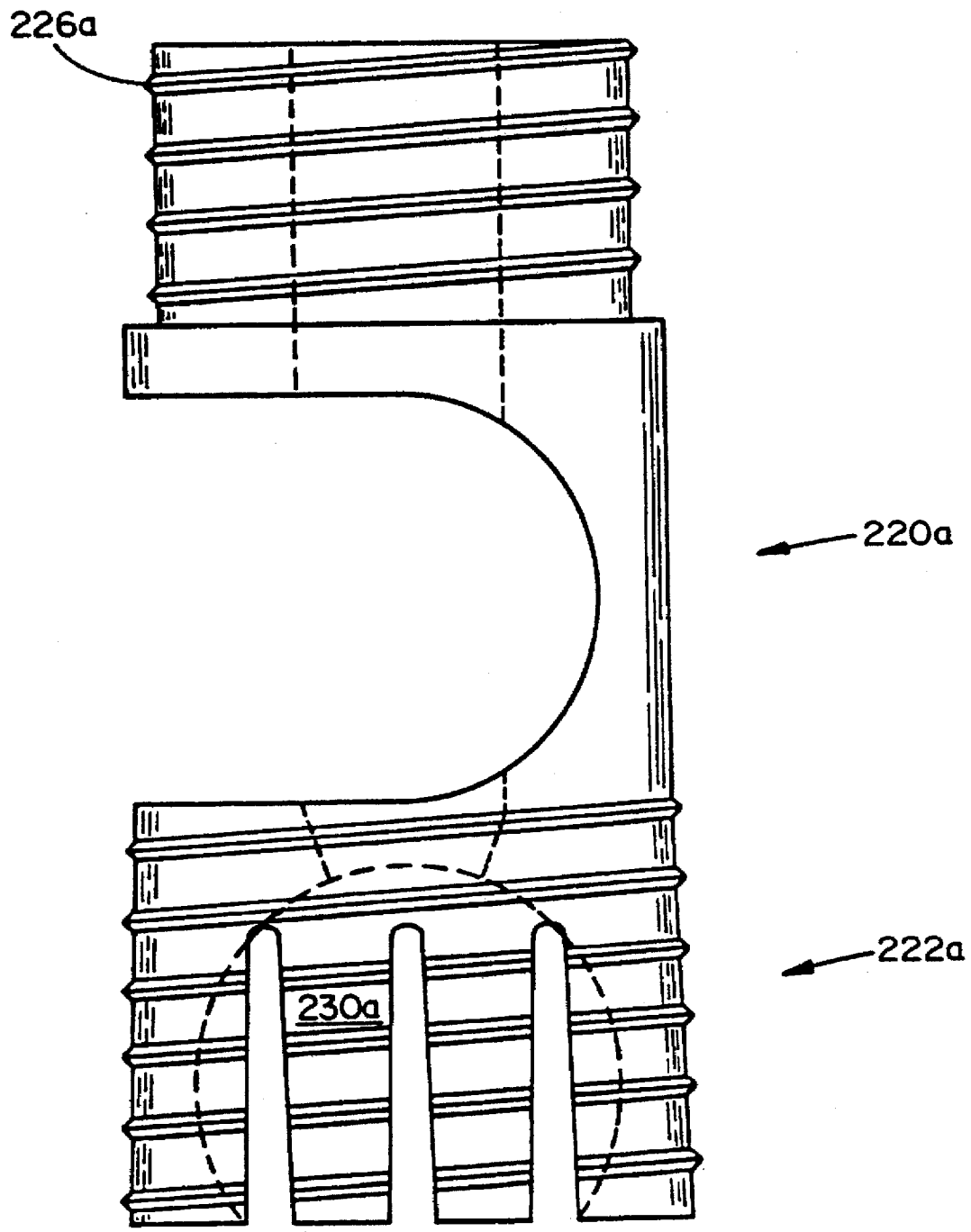
FIGS. 9a and 9b are, respectively, side views of side and top loading coupling elements having a threading on the exterior surface of the lower portions thereof.
Figure 9B:
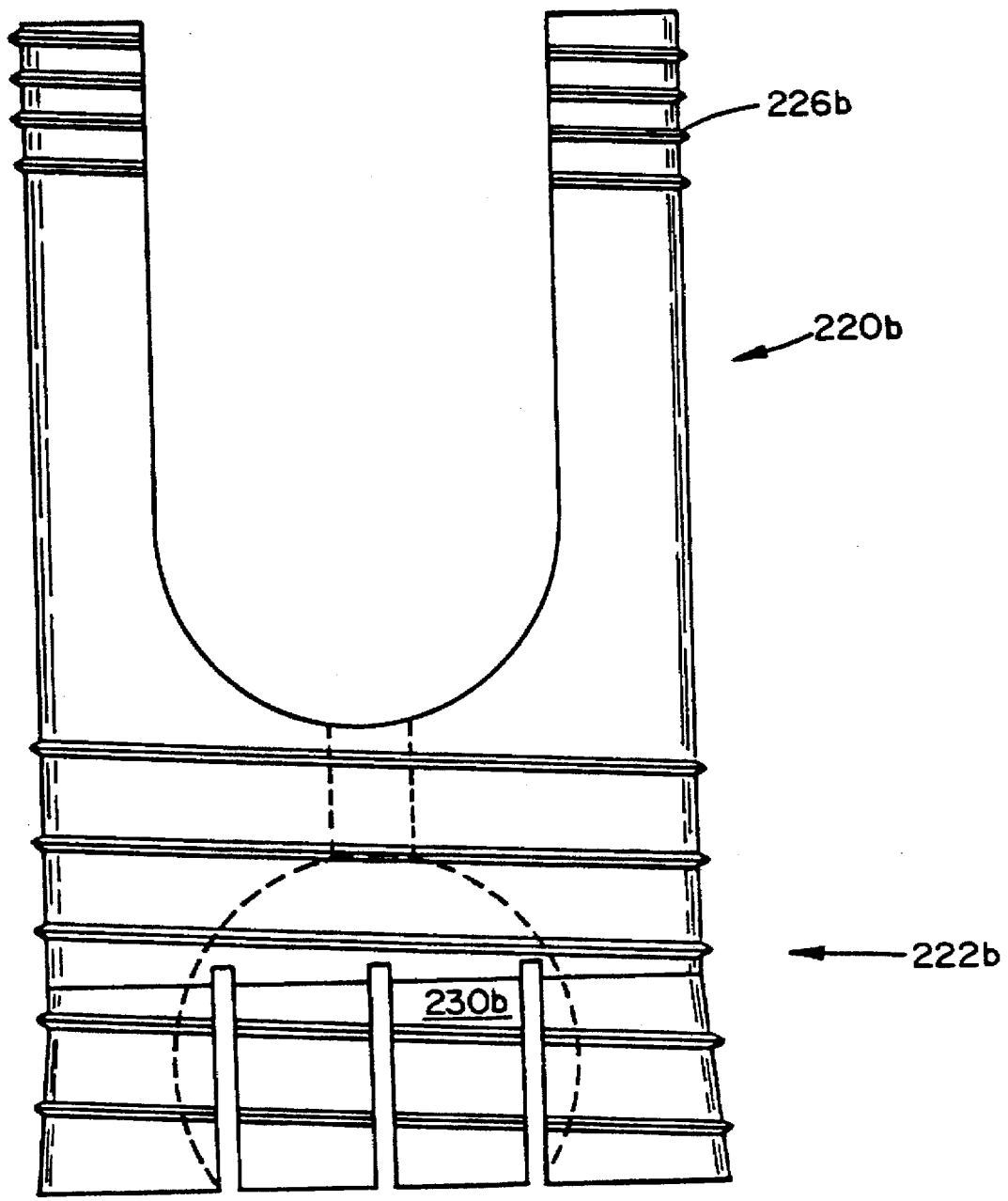
Figure 10:
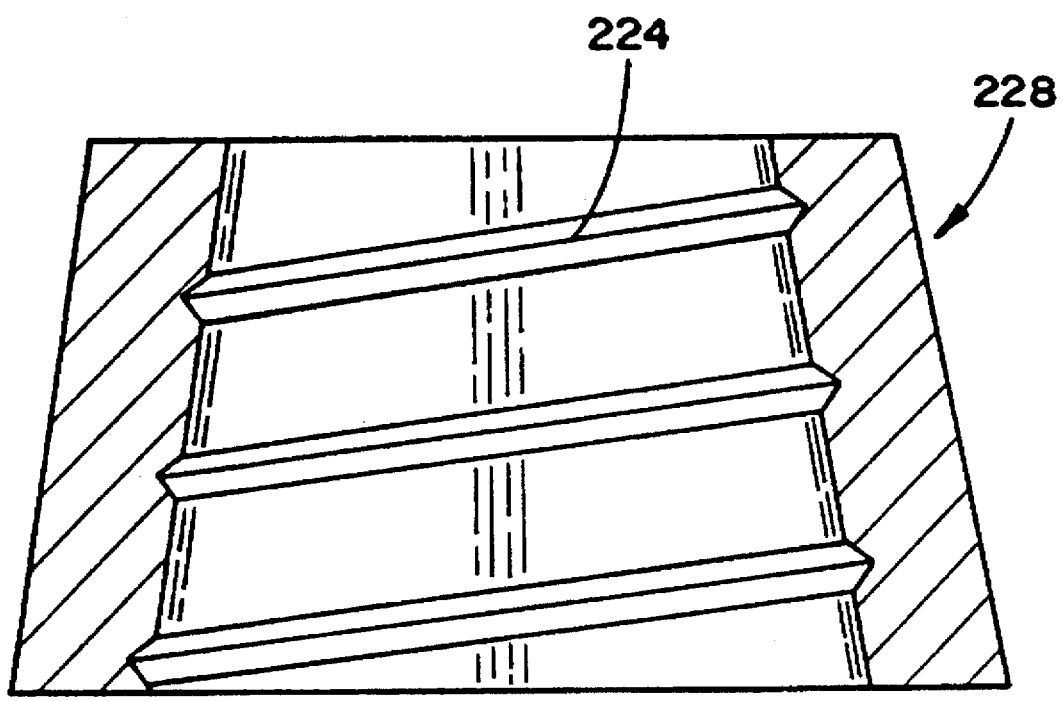
FIG. 10 is a side view of the threaded locking collar which is an aspect of the present invention.

Referring now to FIGS. 9a and 9b, in which two alternative coupling element embodiments of the present invention are shown in side views, a threaded version of the locking mechanism is described. The coupling elements 220a,220b, being side and top loading variations, respectively, are identical to the coupling elements 100a, 100b as set forth hereinabove with reference to FIGS. 1a and 1b, but for the threading 226a,226b disposed on the tapered lower portions 222a,222b thereof. This threading 226a,226b is provided to engage a threading 224 on a locking collar 228, as is illustrated in FIG. 10. This locking collar 228 is identical to the collar 140 set forth hereinabove with reference to FIG. 2, but for the interior threading 224 thereof. It shall be understood that in such an embodiment, the collar 228 is selectively advanceable to lock the head 172,192,206 in the interior volume 230a,230b of the coupling element 220a,220b independent of rod and/or securing sleeve contact therewith While there has been described and illustrated various embodiments of a polyaxial locking mechanism for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A polyaxial locking mechanism for use with orthopaedic implantation apparatus, comprising:

a first element having a curvate head;

a second element, a portion of said element having a tapered exterior surface and a curvate interior surface defining an interior volume for receiving therein said curvate head; and a locking collar having an inner tapered surface mounted around said tapered portion, whereby selected translation of said locking collar relative to said portion causes the mutual engagement of the tapers of the exterior surface of the second element and the inner surface of the locking collar which correspondingly causes said interior surface of said second element to crush lock to said curvate head.

2. The mechanism as set forth in claim 1, wherein said first element comprises a bone screw.

3. The mechanism as set forth in claim 1 wherein said first element comprises a lamina hook.

4. The mechanism as set forth in claim 1, wherein said first element comprises a sacral block.

5. The mechanism as set forth in claim 1, wherein said second element further comprises a rod receiving channel formed therein.

6. The mechanism as set forth in claim 5, wherein said rod receiving channel is formed in the side of said second element.

7. The mechanism as set forth in claim 5, wherein said rod receiving channel is formed in the top of said second element.

8. The mechanism as set forth in claim 5, further comprising means for locking a rod in said rod receiving channel.

9. The mechanism as set forth in claim 8, wherein said locking of said rod in said rod receiving channel causes the selected translation of said locking collar.

10. The mechanism as set forth in claim 1, wherein said locking collar and said tapered portion each further comprise a threading, such that said selected translation of said locking collar is provided by mutual engagement thereof.

* * * * *